United States Patent
Seletskiy et al.

(10) Patent No.: US 8,330,956 B1
(45) Date of Patent: Dec. 11, 2012

(54) OPTICAL COUPLED-CAVITY PHOTO-ACOUSTIC SPECTROSCOPY

(75) Inventors: Denis V. Seletskiy, Albuquerque, NM (US); Michael Hasselbeck, Albuquerque, NM (US); Mansoor Sheik-Bahae, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 325 days.

(21) Appl. No.: 12/791,156

(22) Filed: Jun. 1, 2010

Related U.S. Application Data

(60) Provisional application No. 61/217,511, filed on Jun. 1, 2009.

(51) Int. Cl.
  *G01N 21/00* (2006.01)
  *G01B 11/14* (2006.01)
(52) U.S. Cl. .................. 356/432; 356/622; 356/326
(58) Field of Classification Search .......... 356/432–444, 356/626, 317–319, 326; 372/20, 22, 24.02, 372/50.11, 92
See application file for complete search history.

(56) References Cited

U.S. PATENT DOCUMENTS

| | | | | |
|---|---|---|---|---|
| 3,546,620 A | * | 12/1970 | Kessler et al. | 372/14 |
| 4,498,179 A | * | 2/1985 | Wayne et al. | 372/27 |
| 4,730,105 A | * | 3/1988 | Mitschke et al. | 250/205 |
| 5,132,977 A | * | 7/1992 | Zayhowski et al. | 372/10 |
| 5,251,229 A | * | 10/1993 | Bennett et al. | 372/92 |
| 5,642,375 A | * | 6/1997 | King et al. | 372/97 |
| 5,666,225 A | * | 9/1997 | Colbourne | 359/589 |
| 5,903,347 A | * | 5/1999 | Girvin et al. | 356/339 |
| 6,201,638 B1 | * | 3/2001 | Hall et al. | 359/346 |
| 7,061,946 B2 | * | 6/2006 | Sochava et al. | 372/20 |
| 7,263,871 B2 | * | 9/2007 | Selker et al. | 73/24.02 |
| 7,508,858 B2 | * | 3/2009 | Oktyabrsky et al. | 372/92 |
| 7,573,578 B2 | * | 8/2009 | Zribi et al. | 356/454 |

* cited by examiner

*Primary Examiner* — Sang Nguyen
(74) *Attorney, Agent, or Firm* — MH2 Technology Law Group, LLP

(57) ABSTRACT

Various embodiments provide devices and methods of an optical coupled-cavity photo-acoustic spectroscopy (CC-PAS). The exemplary CC-PAS can include three mirrors configured in parallel to couple a Fabry-Perot (FP) cavity with a sample cavity. The sample cavity can be a resonant cavity for containing a sample. The FP cavity can be used as a tunable input coupler for the sample cavity to improve spectroscopic sensitivities when measuring an absorber in the sample.

19 Claims, 5 Drawing Sheets

OPTICAL COUPLED-CAVITY PHOTO-ACOUSTIC SPECTROSCOPY

RELATED APPLICATIONS

This application claims priority from U.S. Provisional Patent Application Ser. No. 61/217,511, filed Jun. 1, 2009, which is hereby incorporated by reference in its entirety.

GOVERNMENT RIGHTS

This invention was made with Government support under Contract No. FA9550-04-1-0356 awarded by the Air Force Office of Scientific Research (AFOSR). The U.S. Government has certain rights in this invention.

DESCRIPTION OF THE INVENTION

1. Field of the Invention

This invention relates generally to photo-acoustic spectroscopic techniques and, more particularly, to systems and methods for optical coupled-cavity photo-acoustic spectroscopy.

2. Background of the Invention

Spectroscopic techniques are used for sensitive detection of air-borne chemical agents, toxic industrial compounds, and pollutants. Conventional techniques include cavity ring-down, Raman, and photo-acoustic spectroscopy. For example, photo-acoustic spectroscopy (PAS) has been used for small absorbance measurements in gases, liquids and solids. In PAS, optical absorption leads to heating of the medium which in turn causes thermal expansion. If the temperature rise in the medium is faster than the volume can expand, pressure waves (i.e., sound) can be generated and can be detected by a microphone.

Resonant cavity enhancements, for both acoustic and optical waves, have been introduced to enhance PAS sensitivity. For example, optical cavity enhanced PAS techniques couple a laser beam into a resonant cavity to increase the absorbing power. Although cavity-enhanced PAS is dependent on cavity quality, it can be used for real time detection of chemical warfare agents.

FIG. 1 depicts a conventional configuration for an optical cavity enhanced photo-acoustic spectroscopy (PAS). As shown, the conventional cavity enhanced PAS 100 includes a sample placed in a single cavity 110 having reflecting interior surfaces. The single cavity 110 is defined by two mirrors 122 and 124 each having a reflectivity of $R_1$ and $R_2$, respectively.

In the conventional configuration of FIG. 1, the total absorbed power in the cavity 100 from a radiation beam 130 is determined by the following equation:

$$A_T = \frac{(1-R_1)(1+(1-A_s)R_2)A_s}{\left(1-(1-A_s)\sqrt{R_1 R_2}\right)^2} \quad (1)$$

where As denotes a single pass fractional absorbance: $A_s = 1-\exp(-\alpha L)$, with $\alpha(m^{-1})$ denoting absorption coefficient of the sample and L denoting length of the cavity 100. According to Equation (1), an on-resonance condition can be achieved by adjusting the cavity length L to satisfy $L=m\lambda/2n$, wherein m is an integer, n is the refractive index of the medium, and $\lambda$ is wavelength of the radiation beam.

Equation (1) also indicates, when the back mirror 124 is highly reflective, for example, when $R_2 \geq 0.99$, in order to maximize total fraction of the absorbed power, i.e., $A_T=1$, the front mirror 122 can have a reflectivity $R_1$, where $R_1=\exp(-2\alpha L)=(1-A_s)^2$.

Note that for small absorbance with high sensitivity, $A_s \approx \alpha L$, and thus an optimized reflectivity $R_1$ can be $R_1^{opt} \approx 1-2\alpha L$. In this case, optimum input coupling can be obtained with desirable optical impedance matching.

FIG. 2A compares the total absorbance $A_T$ as a function of the front mirror reflectivity $R_1$, when the single pass fractional absorbance $A_s$ are about $10^{-3}$ and about $10^{-4}$, respectively. FIG. 2B compares the total absorbance $A_T$ as a function of the single pass fractional absorbance $A_s$, when two corresponding values of $R_1$ are used. As shown in FIGS. 2A-2B, the total absorbance $A_T$ depends on the input coupling ($R_1$) for a given absorbance ($A_s$). Accordingly, it is desirable to have a tunable input coupler to match for any given absorbance of the sample in the cavity.

SUMMARY OF THE INVENTION

According to various embodiments, the present teachings include a device for spectroscopy. The device can include a coupled-cavity and a radiation source. The coupled-cavity can include a first mirror, a second mirror, and a third mirror configured in parallel with the first mirror and the second mirror forming a Fabry-Perot (FP) cavity, and with the second mirror and the third mirror forming a sample cavity to contain a sample. The radiation source can be configured to generate a radiation beam to pass through both the FP cavity and the sample cavity. The FP cavity can be configured to tune a wavelength of the radiation beam passing through the FP cavity such that the tuned wavelength coincides with an absorption feature of the sample contained in the sample cavity.

According to various embodiments, the present teachings also include a device for photo-acoustic spectroscopy. Specifically, the device can include a coupled-cavity, a radiation source, and a sensor. The coupled-cavity can include a first mirror, a second mirror, and a third mirror configured in parallel to form a Fabry-Perot (FP) cavity by the first mirror and the second mirror, and to form a resonant sample cavity by the second mirror and the third mirror to contain a sample. The radiation source can generate a radiation beam to pass through both the FP cavity and the resonant sample cavity. The FP cavity can be configured to tune a wavelength of the radiation beam passing through the FP cavity. The sensor can be configured to detect pressure waves generated in the resonant sample cavity upon the sample absorbing radiation at the tuned wavelength from the radiation beam passing through the resonant sample cavity. The sensor can convert the detected pressure waves into an electrical signal.

According to various embodiments, the present teachings further include a spectroscopy method. In this method, a Fabry-Perot (FP) cavity can be coupled with a sample cavity by configuring a first mirror, a second mirror, and a third mirror in parallel, wherein the first mirror and the second mirror form the Fabry-Perot (FP) cavity, and the second mirror and the third mirror form the sample cavity. A sample can then be provided in the sample cavity. A radiation beam can be directed to pass through both the FP cavity and the sample cavity such that the FP cavity tunes a wavelength of the radiation beam passing through the FP cavity. Upon the sample absorbing radiation at the tuned wavelength from the radiation beam passing through the sample cavity, the pressure waves generated in the sample cavity can be detected by a sensor, which also converts the detected pressure waves into an electrical signal.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to exemplary embodiments of the invention, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

Various embodiments provide devices and methods for an optical coupled-cavity photo-acoustic spectroscopy (CC-PAS). The exemplary CC-PAS can include three mirrors configured in parallel. A Fabry-Perot (FP) cavity can be defined by a first mirror and a second mirror and can be used as a tunable input coupler. A sample cavity can be defined by the second mirror and a third mirror and can be a resonant cavity for containing a sample. A radiant beam can be tuned by the FP cavity and coupled into the sample cavity. By this configuration, an optimum input coupling and/or an optical impedance matching can be obtained. The optical absorption or the device sensitivity can then be improved, for example, by orders of magnitude, with a sample having low concentrations.

In operation, when a sample in the sample cavity absorbs tuned radiation from the radiant beam, pressure waves can be generated and can be detected by a sensor, for example, a microphone. In embodiments, a detected signal output from the microphone can be processed to determine a concentration of an absorber in the sample. In embodiments, each of the absorber and the sample can be in a form of vapor, gas, liquid and solid.

Figure 1:
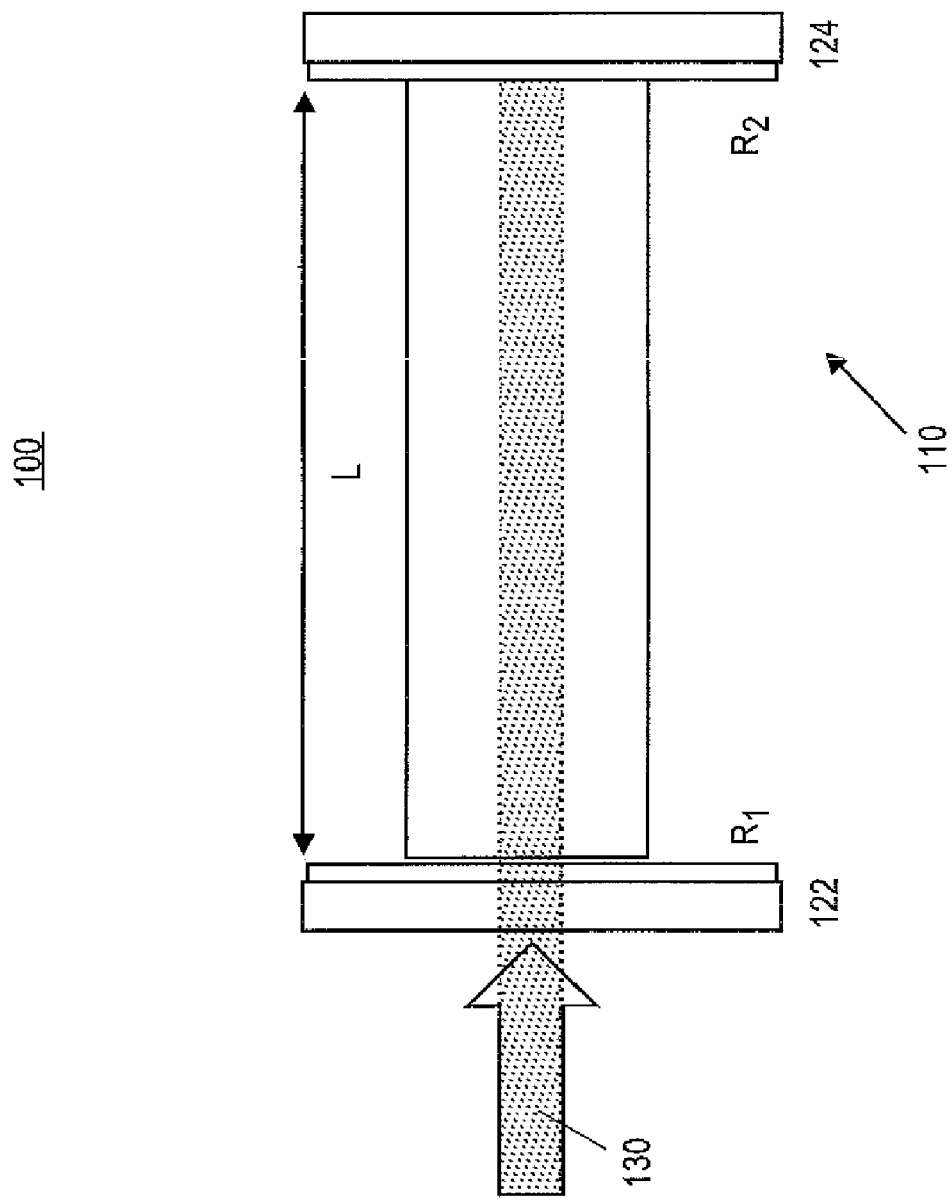
FIG. 1 depicts a conventional configuration for an optical cavity enhanced PAS.
Figure 2A:
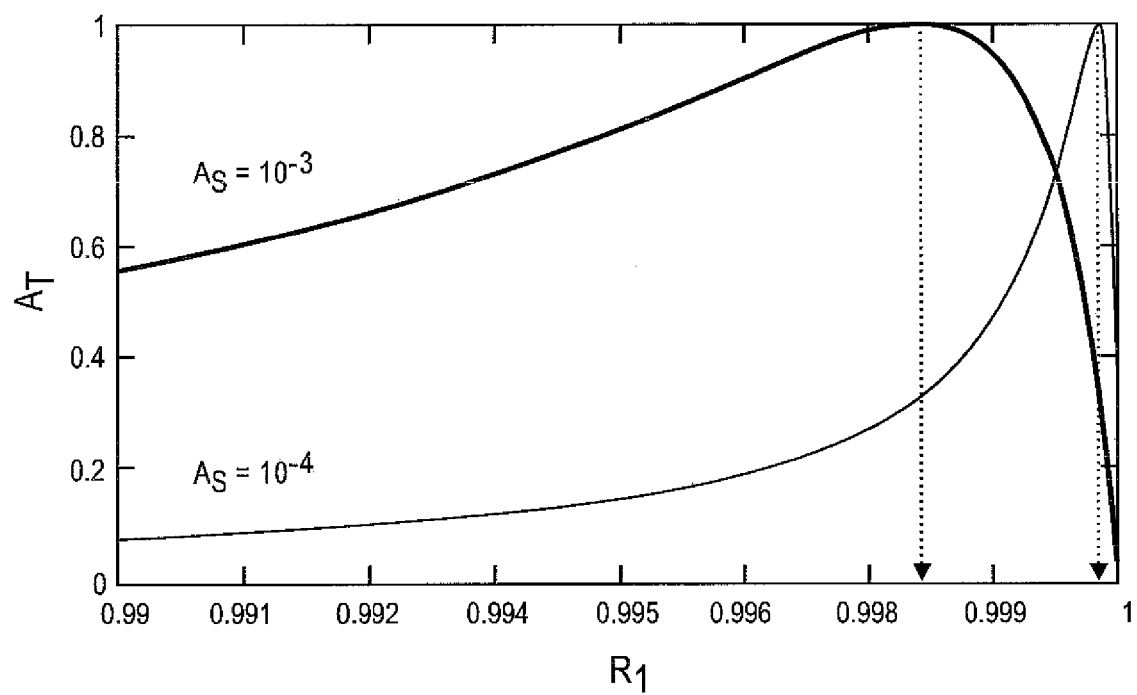
FIGS. 2A-2B depict total absorbed power ($A_T$) in the cavity of FIG. 1 as function of its mirror reflectivity $R_1$ and a single pass fractional absorbance (As), respectively.
Figure 2B:
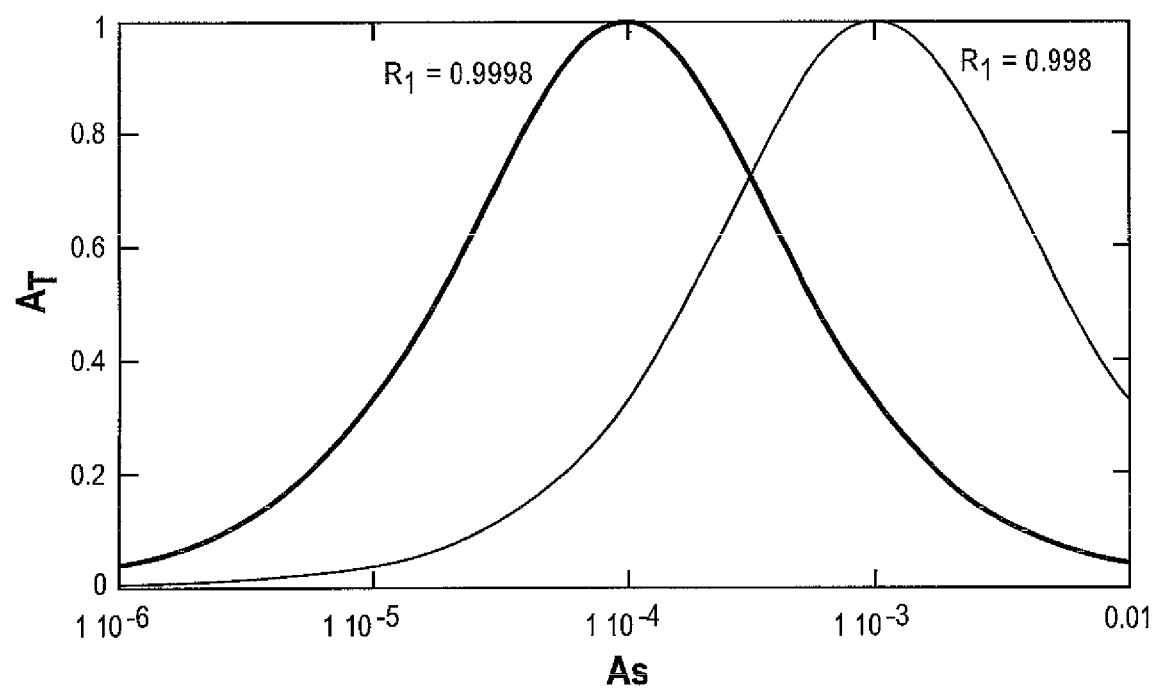
Figure 3:
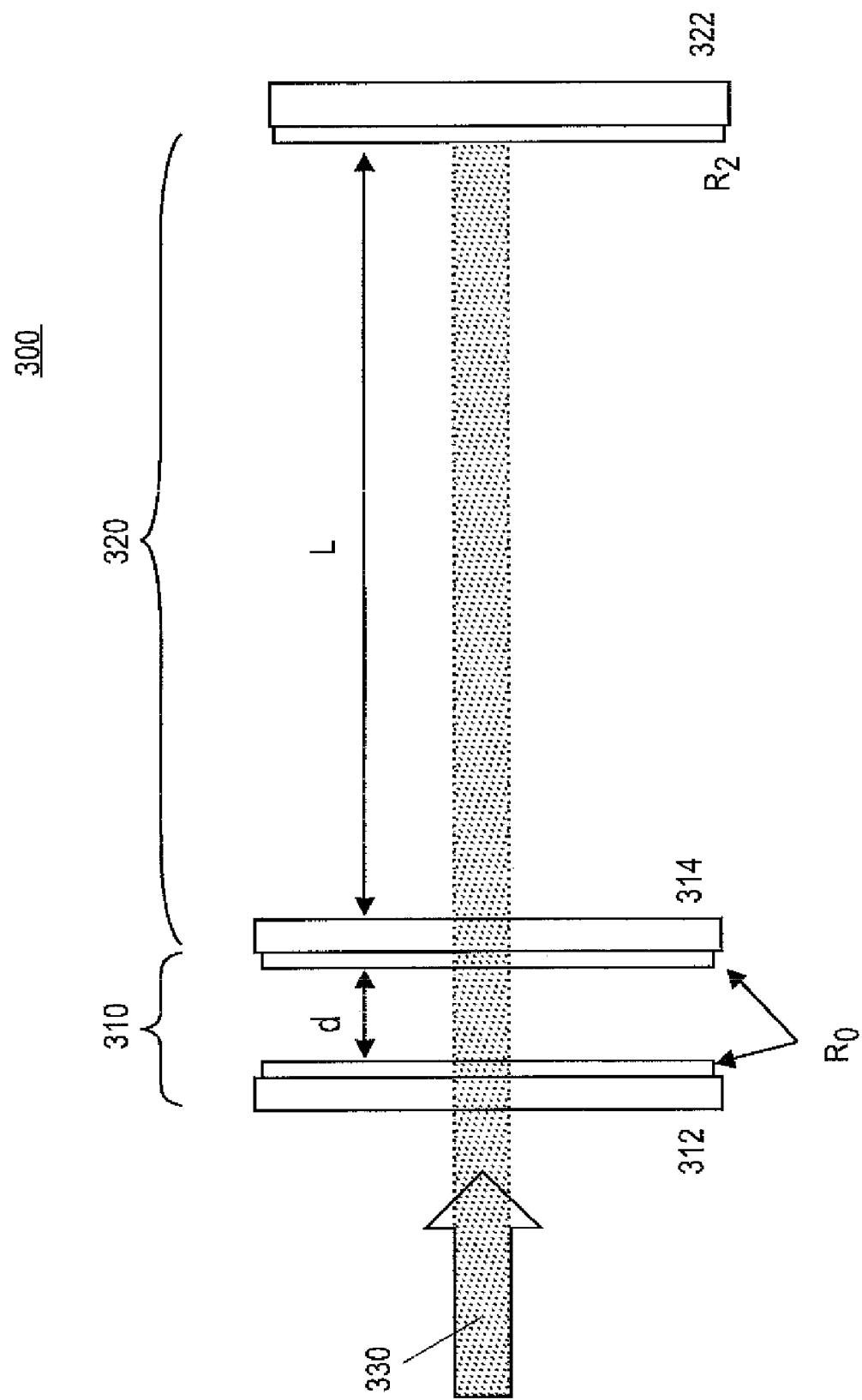
FIG. 3 depicts an exemplary optical coupled-cavity configuration in accordance with various embodiments of the present teachings.

In embodiments, the disclosed tunable input coupler can include a tunable cavity as shown in FIG. 3 to replace the input coupler (see 122 of FIG. 1) in conventional configurations. Specifically, FIG. 3 depicts an exemplary coupled-cavity configuration 300 in accordance with various embodiments of the present teachings.

As shown in FIG. 3, the coupled-cavity configuration 300 can include three mirrors 312, 314, and 322 configured in parallel with a first mirror 312 and a second mirror 314 separated by a distance d and defining a first cavity 310. The first cavity 310 can be coupled with a second cavity 320. The second cavity 320 can be defined by the second mirror 314 and a third mirror 322, which are separated by a cavity length L. The second cavity 320 can be used as a sample cavity. Either of the first cavity and the second cavity can be a resonate cavity.

In embodiments, the distance d between the first mirror 312 and the second mirror 314 of the first cavity 310 can be at least about 10 microns, for example, ranging from about 10 microns to about 100 microns. In embodiments, the length L between the second mirror 314 and the third mirror 322 of the second cavity 320 can range from about 1 mm to about 100 cm, depending on the absorbance requirement.

The first cavity 310 can have reflecting interior surfaces. Each reflecting surface of the mirrors 312 and 314 can have same or different reflectivities. In embodiments, the first cavity 310 can be a symmetric cavity with each reflecting surface having the same reflectivity $R_0$.

In embodiments, the first cavity 310 can include, e.g., a Fabry-Perot (FP) cavity, such as a scanning or passive FP cavity or interferometer. The exemplary FP cavity can have resonance effect and be used to control and measure wavelengths of a radiation beam (see 330) that passes through the FP cavity. The FP cavity can be tunable to provide desired wavelengths or frequencies. The FP cavity can be used as a tunable input coupler for the second cavity 320. The reflectivity $R_1(\delta)$ of the FP cavity (see 310 of FIG. 3) can be described as following:

$$R_1(\delta) = 1 - \frac{1}{1 + F\sin^2(\delta/2)} \quad (2)$$

where $\delta = 2\pi d/\lambda$, and $$F = \frac{4R_0}{(1-R_0)^2},$$

with d denoting spacing between two parallel mirrors 312 and 314, $\lambda$ denoting wavelength of the radiation beam, $R_0$ denoting the same mirror reflectivity of mirrors 312 and 314, and F denoting the coefficient of finesse.

In embodiments, for an optimum input coupling and an optical impedance matching, the reflectivity $R_1(\delta)$ of the FP cavity should be about $(1-2\alpha L)$ according to Equation (1), wherein $\alpha(m^{-1})$ is absorption coefficient of the sample, and L is length of the second cavity. An optimum condition for the configuration of FIG. 3 can then require $F\sin^2(\delta/2) = (2\alpha L)^{-1} - 1$, which results in $F \geq \frac{1}{2}\alpha L$ or $R_0 > 1 - \sqrt{8\alpha L}$. That means, the configuration 300 of FIG. 3 can pose less constraint on mirror fabrication than conventional single cavity configuration of FIG. 1 that requires $R_1 = 1 - 2\alpha L$.

In exemplary embodiments, the reflectivity $R_0$ for the first and the second mirrors 312, 314 can be determined by $R_0 > 1 - \sqrt{8\alpha L}$. Accordingly, if an $\alpha L$ value is about 0.0001, an $R_0$ value of greater than 97.2% can be required. In another example for an $\alpha L$ value of about 0.00001, then $R_0 > 99.1\%$ can be required.

Note that the reflecting surface of the first and second mirrors can be coated with reflecting materials as known to one of ordinary skill in the art. However, the Fresnel reflectivities of the uncoated side of such input coupler cavity mirrors can be considered as "coherent". Thus, these surfaces will not be considered lossy and desired high reflectivities can be achieved. For this reason, each of the mirrors 312 and 314 can be thin and can have a thickness to be minimized to allow for faster movement of the mirror in the active stabilization schemes. Meanwhile, the mirrors 312 and 314 can be structurally sound, i.e. having a thickness to diameter ratio maintained above a certain threshold. For example, for a 1" diameter mirror, a thickness of 1/16" can be desirable.

Figure 4:
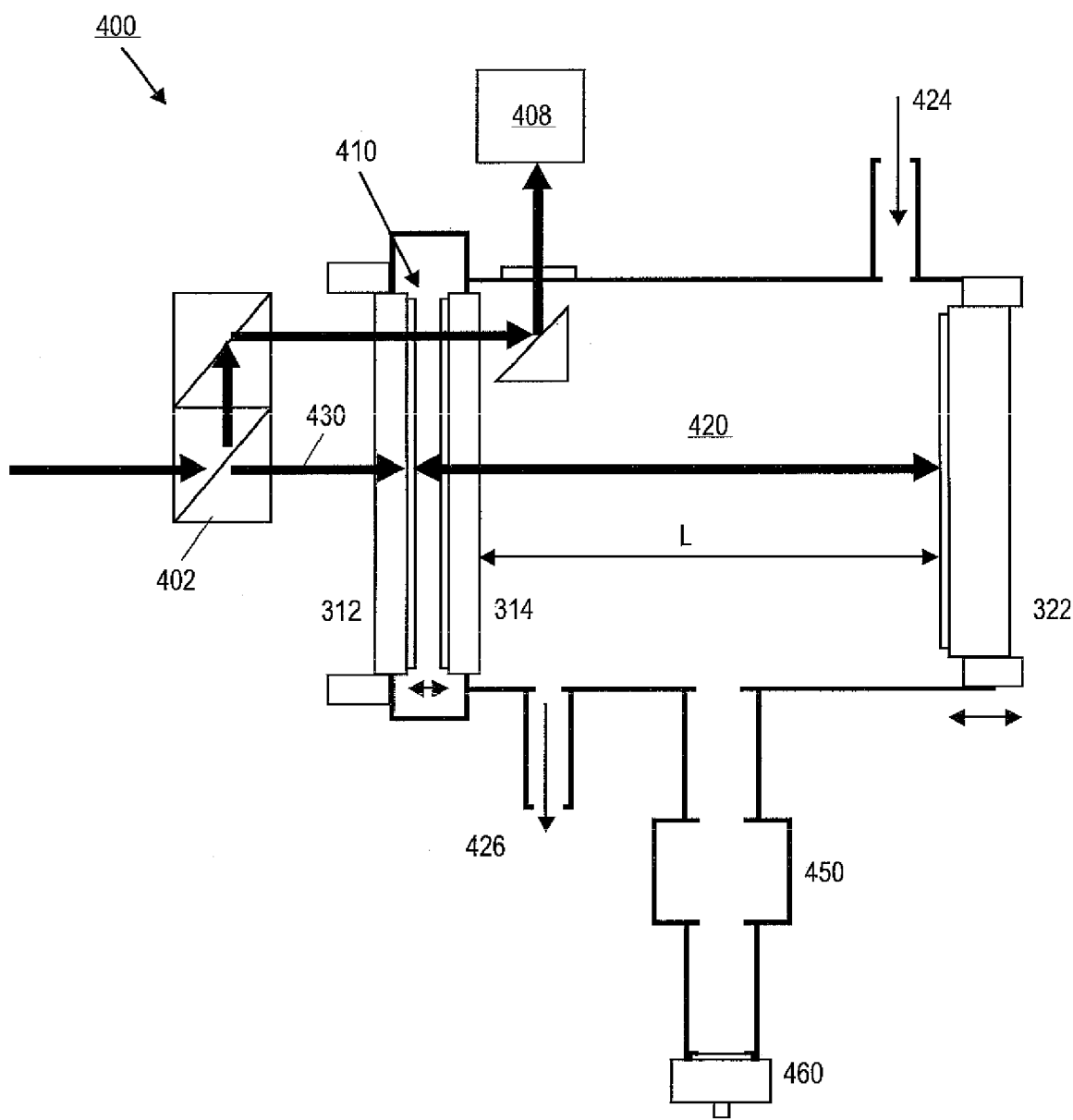
FIG. 4 depicts an exemplary configuration of an optical coupled-cavity PAS in accordance with various embodiments of the present teachings.

FIG. 4 depicts an exemplary optical coupled-cavity photo-acoustic spectroscopy (CC-PAS) 400 using the configuration 300 in accordance with various embodiments of the present teachings.

The exemplary CC-PAS 400 can include a radiation source 402, a coupled-cavity configuration having a FP cavity 410 and a sample cavity 420, a reference detector 408, an acoustic filter 450, and/or a sensor 460.

The radiation source 402 can include, for example, a conventional hot filament, a glow bar, an LED, a laser such as a tunable diode laser, a color center laser, a quantum cascade laser, a vertical-cavity surface-emitting laser (VCSEL), or a horizontal cavity surface emitting laser (HCSEL), and/or any suitable radiation emitter in the wavelength region of interest.

The radiation source 402 can be configured to generate a radiation beam 430 directed to pass through the FP cavity 410 and further coupled into the sample cavity 420. The radiation beam 430 can also be directed onto the reference detector 408. The reference detector 408 can be configured inside the sample cavity 420. The reference detector 408 can provide, e.g., a frequency of the radiation beam as a reference to calibrate the input coupler reflectivity $[R_1(\delta)]$ of the FP cavity 410. This can allow accurate measurements of the absorbance magnitude.

When the radiation beam 430 from the radiation source 402 passes through, the FP cavity 410 can tune the radiation across a desirable wavelength range. The tuned radiation beam can then be directed through the sample in the sample cavity 420. The tuned wavelength by the FP cavity 410 can coincide with the absorption feature of the sample in the sample cavity 420. In embodiments, the sample can include an absorber that absorbs radiation at tunable wavelengths by the FP cavity 410 from the radiation beam. In embodiments, more than one radiation source 402 can be utilized to provide a range of tunable wavelengths.

In embodiments, the absorber can include, but is not limited to, water vapor, trace gases either chemical or biological. In embodiments, due to the coupling of the FP cavity, trace amounts of absorbers can be detected with high selectivity or sensitivity. For example, the absorber concentration to be detected can be less than or equal to approximately 1 ppm and/or less than or equal to approximately $10^{-4}$%.

In embodiments, as exemplarily shown in FIG. 4, a gas sample can be directed into the sample cavity 420 via an inlet 424 and flushed from the sample cavity 420 via an outlet 426. In some variations, the inlet 424 and the outlet 426 can include valves that can seal the inner volume of the sample cavity 420 to obtain a static measurement of a fixed volume of sample. In embodiments, if there are no inlet and outlet valves, or if the inlet and outlet valves are open, the system can be used in a continuous or semi-continuous flow mode, for example to continuously or semi-continuously monitor the concentration of a target gas, analyte or any absorber in a flowing gas stream.

In an exemplary embodiment, the FP cavity can tune the radiation beam having at least a wavelength where a gas (e.g., a water vapor) absorption can be resolved from a gas background absorption (e.g., a refrigerant gas).

In embodiments, the tuned radiation beam by the FP cavity 410 can have a frequency that substantially matches a resonance frequency of the sample cavity 420.

With the exemplary photo-acoustic spectroscopic configuration of FIGS. 3-4, energy absorbed by absorbers or any target molecules can result in the rise of gas temperature in the sample cavity 420. Temperature fluctuations can produce a pressure wave (i.e., sound), which can be detected by a suitable sensor 460, for example, a microphone.

In embodiments, the acoustic cavity or filter 450 can be configured between the sample cavity 420 and the sensor 460. The acoustic filter 450 can be used to reduce the level of noise. The acoustic filter 450 can have a hollow space, in which pressure waves or sound can exist.

The sensor 460 can be an acoustic-to-electric transducer or a microphone that converts the pressure waves into an electrical signal. The absorption at the tuned wavelength can be determined by the sensor 460, which can provide an electronic output signal, for example, to a microprocessor (not shown) where the concentration can be computed. By measuring pressure at different wavelengths, a photo-acoustic spectrum of the absorbers or target molecules can be obtained to determine the concentration.

In embodiments, the exemplary configurations in FIGS. 3-4 can also be used for an active optical impedance matching of laser cooling systems and methods using ytterbium-doped fluorozirconate glass, as disclosed in related journal publications of Applied Physics Letters 96, 181106 (2010), entitled "Resonant Cavity-Enhanced Absorption for Optical Refrigeration," which is hereby incorporated by reference in its entirety.

While the invention has been illustrated with respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." As used herein, the term "one or more of" with respect to a listing of items such as, for example, A and B, means A alone, B alone, or A and B. The term "at least one of" is used to mean one or more of the listed items can be selected.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume values as defined earlier plus negative values, e.g. −1, −1.2, −1.89, −2, −2.5, −3, −10, −20, −30, etc.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for spectroscopy comprising:
a coupled-cavity comprising a first mirror, a second mirror, and a third mirror configured in parallel, wherein the first mirror and the second mirror form a Fabry Perot (FP) cavity, and the second mirror and the third mirror form a sample cavity configured to contain a sample; and
a radiation source configured to generate a radiation beam to pass through both the FP cavity and the sample cavity, wherein the FP cavity is configured to tune a wavelength of the radiation beam passing through the FP cavity such that the tuned wavelength coincides with an absorption feature of the sample contained in the sample cavity,
wherein each of the first mirror and the second mirror has a same reflectivity $R_0$, wherein $R_0 > 1 - \sqrt{8\alpha L}$; $\alpha$ is the sample's absorption coefficient; and L is the sample cavity's length.

2. The device of claim 1, wherein a distance d between the first mirror and the second mirror of the FP cavity ranges from about 10 microns to about 100 microns.

3. The device of claim 1, wherein a length L between the second mirror and the third mirror of the sample cavity ranges from about 1 millimeter to about 100 centimeters.

4. The device of claim 1, wherein each of the first mirror and the second mirror of the FP cavity comprises a mirror having a diameter of about 1" and a thickness of about 1/16".

5. The device of claim 1, wherein each of the FP cavity and the sample cavity is a resonant cavity.

6. The device of claim 1, wherein the radiation source comprises a hot filament, a glow bar, an LED, or a laser.

7. A device for photo-acoustic spectroscopy comprising:
a coupled-cavity comprising a first mirror, a second mirror, and a third mirror configured in parallel, wherein the first mirror and the second mirror form a Fabry-Perot (FP) cavity, and the second mirror and the third mirror form a resonant sample cavity configured to contain a sample;
a radiation source that generates a radiation beam to pass through both the FP cavity and the resonant sample cavity, wherein the FP cavity is configured to tune a wavelength of the radiation beam passing through the FP cavity; and
a sensor configured to detect pressure waves generated in the resonant sample cavity upon the sample absorbing radiation at the tuned wavelength from the radiation beam passing through the resonant sample cavity; wherein the sensor converts the detected pressure waves into an electrical signal.

8. The device of claim 7, wherein each of the first mirror and the second mirror has a same reflectivity $R_0$, wherein $R_0 > 1 - \sqrt{8\alpha L}$; $\alpha$ is absorption coefficient of the absorber; and L is length of the resonant sample cavity.

9. The device of claim 7, wherein a length L between the second mirror and the third mirror of the sample cavity ranges from about 1 mm to about 100 cm.

10. The device of claim 7, wherein a distance d between the first mirror and the second mirror of the FP cavity ranges from about 10 microns to about 100 microns.

11. The device of claim 7 further comprising a reference detector positioned in the resonant sample cavity; wherein the generated radiation beam is directed onto the reference detector to calibrate a reflectivity of the FP cavity.

12. The device of claim 7 further comprising an acoustic filter configured between the resonant sample cavity and the sensor; wherein the sensor comprises a microphone.

13. A spectroscopy method comprising:
coupling a Fabry-Perot (FP) cavity with a sample cavity by configuring a first mirror, a second mirror, and a third mirror in parallel, wherein the first mirror and the second mirror form the Fabry-Perot (FP) cavity, and the second mirror and the third mirror form the sample cavity;
providing a sample in the sample cavity;
directing a radiation beam to pass through both the FP cavity and the sample cavity, wherein the FP cavity tunes a wavelength of the radiation beam passing through the FP cavity; and
detecting pressure waves generated in the sample cavity by a sensor, upon the sample absorbing radiation at the tuned wavelength from the radiation beam passing through the sample cavity; wherein the sensor converts the detected pressure waves into an electrical signal.

14. The method of claim 13, wherein the radiation beam tuned by the FP cavity has a frequency that substantially matches a resonance frequency of the sample cavity.

15. The method of claim 13 further comprising processing the electrical signal from the sensor to determine a concentration value of an absorber in the sample.

16. The method of claim 13 further comprising detecting an absorber in the sample, wherein each of the absorber and the sample is in a form comprising vapor, gas, liquid or solid.

17. The method of claim 13 further comprising detecting an absorber having a concentration of about 1 ppm or less, or about $10^{-4}$% or less in the sample.

18. The method of claim 13, wherein each of the FP cavity and the sample cavity is a resonant cavity, wherein the sample cavity has a cavity length L between the second mirror and the third mirror ranging from about 1 mm to about 100 cm.

19. The method of claim 13, wherein each of the first mirror and the second mirror has a same reflectivity $R_0$, wherein $R_0 > 1 - \sqrt{8\alpha L}$; $\alpha$ is absorption coefficient of the absorber; and L is length of the sample cavity.

* * * * *